(12) United States Patent
Ng et al.

(10) Patent No.: US 11,799,322 B2
(45) Date of Patent: *Oct. 24, 2023

(54) WIRELESS CHARGING SYSTEM FOR MEDICAL DEVICES

(71) Applicant: COVIDIEN AG, Neuhausen am Rheinfall (CH)

(72) Inventors: Michael Ng, Kowloon (HK); Peter Douglas Colin Inglis, Boulder, CO (US); Jurgen Van Vlem, Kowloon (HK); Jakob Struik, Yeun Long (HK)

(73) Assignee: COVIDIEN AG

( * ) Notice: Subject to any disclaimer, the term of this patent is extended or adjusted under 35 U.S.C. 154(b) by 0 days.

This patent is subject to a terminal disclaimer.

(21) Appl. No.: 17/962,230

(22) Filed: Oct. 7, 2022

(65) Prior Publication Data

US 2023/0029630 A1    Feb. 2, 2023

Related U.S. Application Data

(63) Continuation of application No. 17/165,101, filed on Feb. 2, 2021, now Pat. No. 11,502,546.

(60) Provisional application No. 62/977,517, filed on Feb. 17, 2020.

(51) Int. Cl.
*H01M 10/46*    (2006.01)
*H02J 50/10*    (2016.01)
*H02J 50/40*    (2016.01)
*H02J 50/70*    (2016.01)
*H01F 27/36*    (2006.01)
*H02J 7/00*     (2006.01)
*H02J 7/02*     (2016.01)
*A61B 1/00*     (2006.01)
*A61B 1/267*    (2006.01)

(52) U.S. Cl.
CPC ............ *H02J 50/10* (2016.02); *H01F 27/366* (2020.08); *H02J 7/0013* (2013.01); *H02J 7/0044* (2013.01); *H02J 7/0047* (2013.01); *H02J 7/02* (2013.01); *H02J 50/40* (2016.02); *H02J 50/70* (2016.02); *A61B 1/00029* (2013.01); *A61B 1/00034* (2013.01); *A61B 1/267* (2013.01)

(58) Field of Classification Search
CPC .. H02J 50/10; H02J 50/40; H02J 50/70; H02J 50/005; H02J 7/0013; H02J 7/0044; H02J 7/0047; H02J 7/02; H02J 7/0045; H02J 7/0042; H02J 2310/23; A61B 1/267; A61B 1/00034; A61B 1/00029; H01F 27/366
USPC .......................... 320/104, 108, 110, 114, 115
See application file for complete search history.

(56) References Cited

U.S. PATENT DOCUMENTS 11,502,546 B2 * 11/2022 Ng ........................ H02J 50/10

* cited by examiner

*Primary Examiner* — Edward Tso

(57) ABSTRACT

A wireless charging system for recharging batteries in a medical environment includes a charging station. The charging station may include an opening to receive batteries and an outlet for dispensing charged batteries, wherein the outlet comprises a slot in a front cover. The charging station also includes a wireless power transmitter having a transmitting antenna.

15 Claims, 9 Drawing Sheets

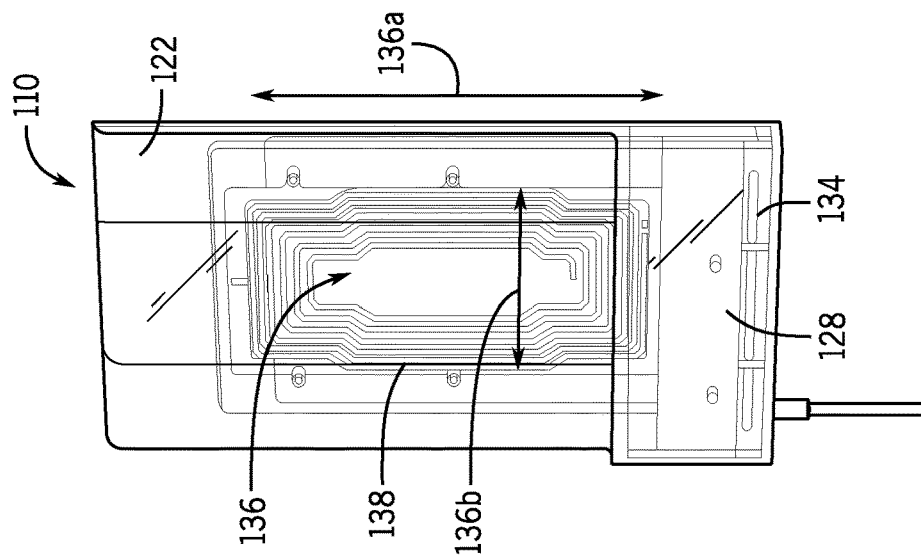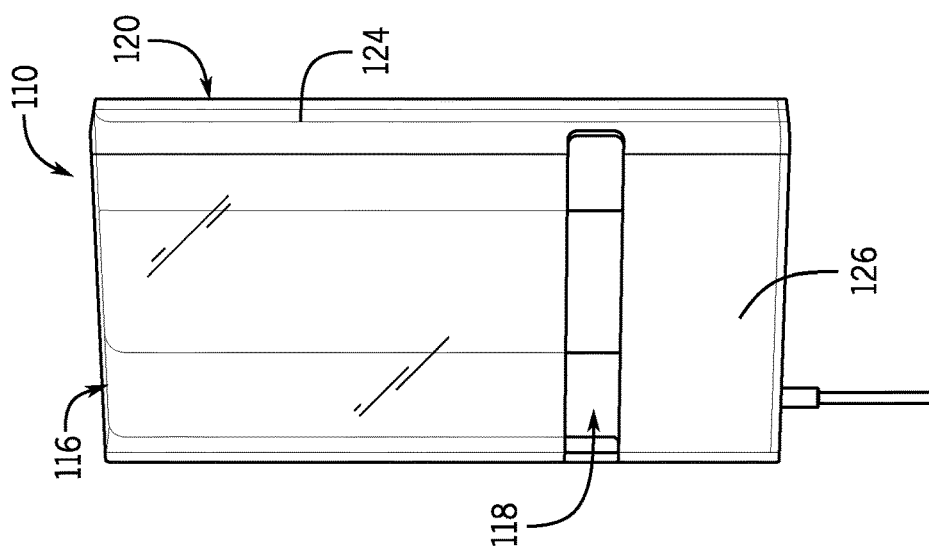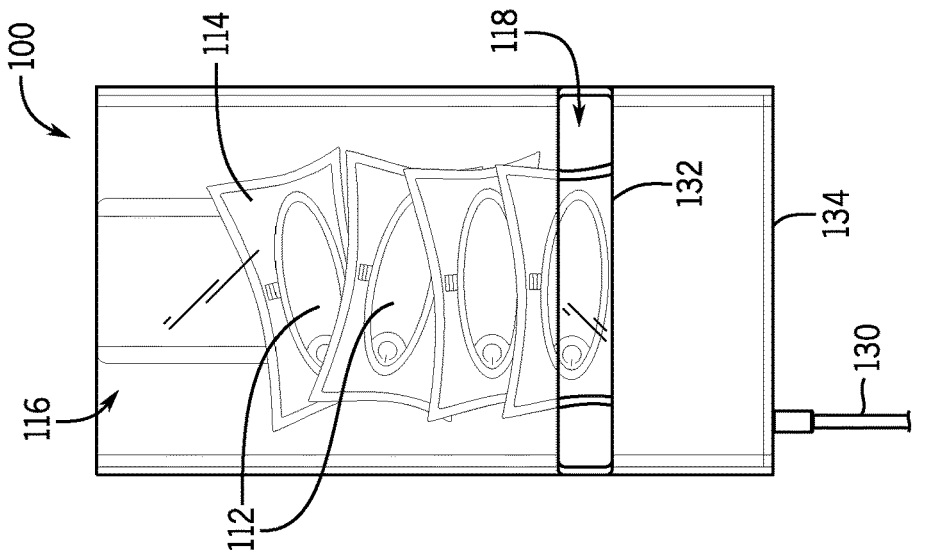

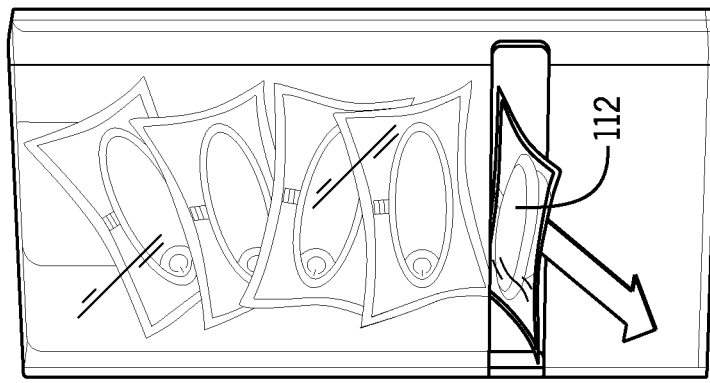
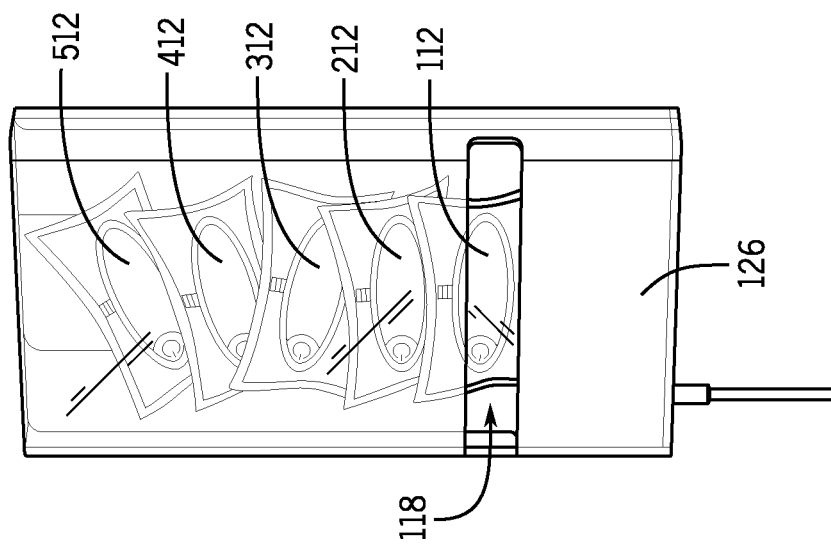
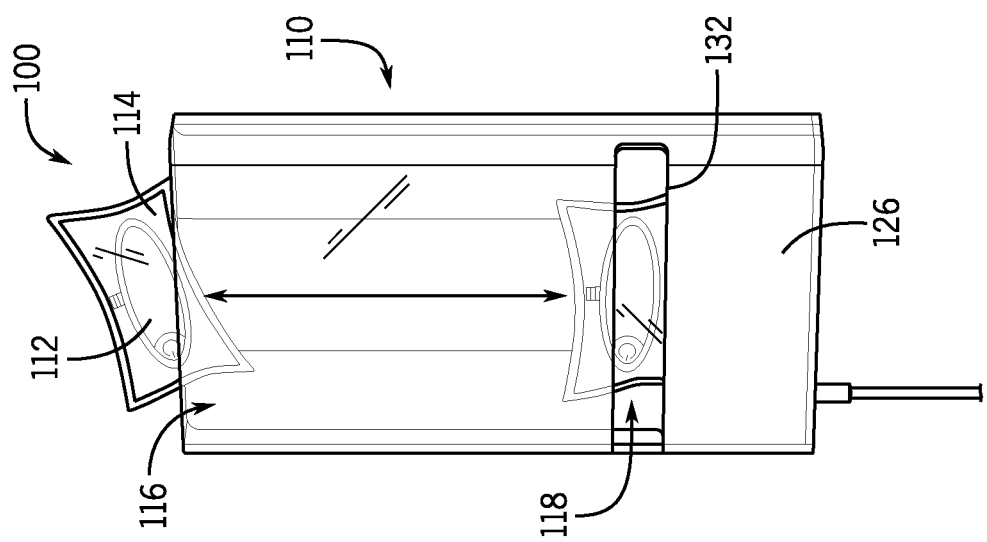

WIRELESS CHARGING SYSTEM FOR MEDICAL DEVICES

CROSS-REFERENCE TO RELATED APPLICATIONS

The present application is a continuation of U.S. application Ser. No. 17/165,101 filed Feb. 2, 2021, which claims the benefit of U.S. Provisional Application No. 62/977,517, filed on Feb. 17, 2020, the disclosures of which are incorporated herein by reference in their entireties. To the extent appropriate a claim of priority is made to each of the above disclosed applications.

BACKGROUND

The present disclosure relates generally to medical devices and, more particularly, to a battery charging system for wirelessly charging batteries across a sterile barrier in a medical environment.

Medical environments such as hospitals, surgery centers, urgent care centers, clinical care centers, and others utilize batteries to power devices such as scopes, cameras, surgical tools, and various powered tools and accessories. Often these devices need to be cleaned, sanitized, or sterilized prior to use or between uses. Recharging the batteries in these devices presents a challenge in medical environments. The remainder of this disclosure addresses solutions in this field.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In one embodiment, a wireless charging system for recharging batteries in a medical environment includes a charging station. The charging station includes a housing comprising a rear plate, a slidable front cover, and a base; an inlet for depleted batteries at a top of the housing, wherein the inlet comprises an opening between the rear plate and the slidable front cover an outlet for charged batteries below the inlet, wherein the outlet comprises a slot in the front slidable cover; a vertical channel extending between the inlet and outlet; a wireless power transmitter inside the rear plate, wherein the wireless power transmitter comprises a transmitting antenna; a status light on the housing; and a power supply connected to the housing. The wireless charging system also includes at least two rechargeable batteries in different orientations inside the vertical channel, each battery having a wireless power receiver which comprises a receiving antenna, and each battery sealed inside a sterile barrier, wherein the transmitting antenna has a vertical length that is longer than a horizontal width, and wherein the horizontal width increases in a middle section of the transmitting antenna to create a bulged shape, the transmitting antenna sized to charge the at least two rechargeable batteries simultaneously in the different orientations.

In one embodiment, a charging station for recharging batteries in a medical environment includes a housing comprising an inlet for batteries at a top of the housing, an outlet for charged batteries below the inlet, and a vertical channel extending between the inlet and outlet; a wireless power transmitter inside the housing, wherein the wireless power transmitter comprises a transmitting antenna configured to wirelessly charge a plurality of rechargeable batteries simultaneously by transmitting wireless power to a wireless power receiver of each of the plurality of batteries, and wherein the transmitting antenna, in operation, charges the plurality of batteries independent of orientation in the charging station; a status light on the housing; and a power supply connected to the housing.

A method for wirelessly recharging batteries inside a sterile barrier includes the steps of receiving a first battery through an inlet at a top of a charging station, the first battery sealed inside a first sterile barrier; receiving a second battery through the inlet and onto the first battery to form a stack of batteries inside the charging station, the second battery sealed inside a second sterile barrier; transmitting power wirelessly to the first battery through the first sterile barrier and simultaneously transmitting power wirelessly to the second battery through the second sterile barrier; providing the first battery in a charged state through an outlet at a bottom of the charging station; and subsequently, providing the second battery in a charged state through the outlet.

BRIEF DESCRIPTION OF THE DRAWINGS

Advantages of the disclosed techniques may become apparent upon reading the following detailed description and upon reference to the drawings in which:

FIG. 1 is a front view of a wireless charging system according to an embodiment of the present disclosure.

FIG. 2 is a perspective view of a charging station according to an embodiment of the present disclosure.

FIG. 3 is a perspective view of internal components of the charging station of FIG. 2.

FIG. 4 is a perspective view of a battery insertion in the wireless charging system according to an embodiment of the present disclosure.

FIG. 5 is a perspective view of the wireless charging system with multiple batteries inserted according to an embodiment of the present disclosure.

FIG. 6 is a perspective view of removal of a battery from the wireless charging system according to an embodiment of the present disclosure.

DETAILED DESCRIPTION OF SPECIFIC EMBODIMENTS

Figure 8:
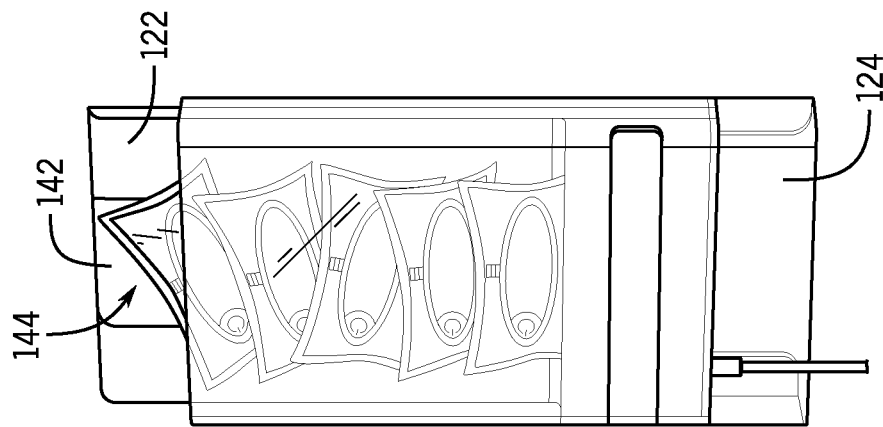
FIG. 8 is a perspective view of a wireless charging system with a sliding removable cover, according to an embodiment of the present disclosure.

The present disclosure relates generally to medical devices and, more particularly, to a battery charging system for wirelessly charging batteries across a sterile barrier in a medical environment. A wireless charging system 100 according to an embodiment is depicted in FIG. 1. The wireless charging system 100 includes a charging station 110 and several rechargeable batteries 112. Each battery is sealed inside a sterile barrier 114. However, the wireless charging system 100 is also capable of charging batteries 112 that are not sealed within a sterile barrier 114. The charging station 110 transmits power wirelessly to the batteries 112 across the sterile barrier 114, so that the batteries do not need to be sterilized again after charging. The batteries enter the charging station through an inlet 116 at the top and then exit the charging station at an outlet 118 at the bottom in a first-in first-out order, such that the battery that entered first exits first. This ordering dispenses batteries 112 in order of the amount of time they have spent inside the charging station 110, to reduce the chance that a battery 112 is removed from the station 110 before it has had time to charge.

As shown in FIG. 1, the batteries 112 are oriented generally horizontally inside the charging station, forming a vertical stack of batteries that move from the inlet 116 toward the outlet 118 as batteries at the outlet are taken for use. The batteries 112 can receive power wirelessly regardless of their orientation inside the charging station 110; charging a battery 112 inside the charging station 110 is not dependent on any particular orientation (turned, tilted, rotated, etc.) of the battery 112. The stacked batteries 112 can all have a same general orientation within the charging station 110, or some or all of the batteries 112 can have different orientations relative to other batteries 112. Regardless, the charging station 101, in operation, charges the batteries independent of their orientation within the charging station 110. In addition, the charging station 110 can be mounted or arranged in other orientations and charge the batteries 112.

The charging station 110 is shown in FIG. 2 in an empty or unloaded state without any batteries 112 that are being charged. In an embodiment, the charging station 110 includes a housing 120 with a rear plate 122, a front cover 124, and a base 126. The base 126 includes or is attached to a power supply such as a battery, a power generator, or a power cord 130 (which attaches to an external power supply such as a wall outlet). The inlet 116 is an opening formed between the front cover 124 and the rear plate 122. The outlet 118 is formed as a horizontal slot in the front cover, below the inlet 116 and above the base 126. The top of the base 126 can also serve as a tray 132 on which the batteries rest. The housing 120 also includes an indicator light 134, such as a vertical or horizontal light bar or shaped light indicator (e.g., circle, star, triangle), LED light or strip, illuminated surface, or other suitable visible indicator. In FIGS. 1-3, the indicator light 134 is a horizontal light bar at the bottom of the base 126.

FIG. 3 also shows some internal components of the charging station 110. A wireless power transmitter 136 is located inside the rear plate 122. In an embodiment, the wireless power transmitter 136 includes a transmitting antenna formed on a printed circuit board (PCB). The charging station 110 also includes a main board 128 in the base 126. The main board 128 includes a processor, memory, and other components for operating the charging station 110.

The power transmitter 136 transmits power wirelessly to the batteries 112 inside the charging station. As shown in more detail in FIG. 14 (and described below), each battery includes a power receiver 140 such as a receiving antenna, that receives the wirelessly-transmitted power and stores it in a battery cell 142. The power transmitter 136 is designed to send power wirelessly to multiple batteries 112 at the same time. Referring to FIGS. 1-3, in an embodiment the charging station 110 can charge at least four batteries 112 simultaneously. The charging station 110 has a shape that is large enough to contain at least four batteries 112 inside the charging station, and the power transmitter 136 is sized to transmit power to these four batteries simultaneously, so that the four batteries are all receiving power at the same time. This is accomplished by the relative sizing and orientation of the power transmitter 136 and the power receivers 140. In an embodiment, both the power transmitter 136 and the power receivers 140 are elongated, meaning that they have one dimension longer than the other. The power transmitter 136 is oriented inside the rear plate 122 such that the longer dimension 136a is vertical, and the shorter dimension 136b is horizontal. This shape and orientation of the power transmitter 136 creates a charging field (such as a magnetic field) inside the charging station, and the batteries 112 pass through the charging field as they pass through the charging station. In an embodiment, the batteries are oriented such that their longer dimension is generally horizontal (see FIG. 1). This enables at least four batteries 112 to fit inside the charging field created by the power transmitter 136. However, the batteries 112 receive charge in any orientation inside the charging field.

Although four batteries are shown in FIG. 1, in other embodiments, different numbers of batteries can be charged simultaneously, such as two, three, five, six, seven, eight, nine, ten, or more batteries.

Referring again to FIG. 3, the power transmitter 136 has a rectangular shape, taller than wide, with a bulge 138 in the middle. The shorter dimension 136b of the power transmitter widens in the center, to create the bulge 138. This bulged shape compensates for the loss in strength of the charging field along the long dimension of the rectangle. The charging field is relatively stronger at the corners of the rectangle (of the power transmitting antenna), and the field is relatively weaker along the longer ends. Thus, a rectangular charging antenna creates a charging field with an hourglass shape (narrower in the middle). The bulge 138 is a reverse hourglass shape, which compensates for the shape of the charging field and creates a more uniform charging field along the length of the charging antenna.

In an embodiment, the transmitting antenna on the power transmitter 136 has a horizontal length 136b that is longer than the longest dimension of the receiving antenna 140 in the battery 112. This shape creates a charging field that is bigger than the battery's receiving antenna, and the battery 112 can receive charge in any orientation inside the charging station. The battery 112 can be rotated or turned in any orientation inside the charging station 110 and still effectively receive power to charge the battery. As shown in FIG. 1, the batteries 112 in the stack of batteries are tilted in different directions, away from horizontal, and they are all receiving power simultaneously. The batteries 112 do not need to be aligned in a particular way in order to receive charge in the charging station 110. They can face in toward the plate 122 or out toward the cover 124. In an embodiment, the charging station is sized and shaped to receive the batteries in a generally horizontal orientation so that the batteries rest in a vertical stack inside the charging station and arrive at the outlet in a first-in first-out order. However if a battery moves through the charging station in a different orientation (vertical, or tilted), it will still receive power. The battery can be dropped into the charging station quickly and easily, without needing to be precisely aligned.

An example of a wireless charging system 100 in use is shown in FIGS. 4-6. In FIG. 4, a first battery 112 in a depleted state is deposited into the charging station 110 through the inlet 116 at the top. If the charging station 110 is empty, the first battery 112 passes through the charging station to the base 126, where it rests on the tray 132. If the charging station 110 is turned on and operating, it transmits power wirelessly to the first battery 112.

In FIG. 5, additional batteries 212, 312, 412, 512 are inserted into the charging station through the inlet 116, forming a vertical stack of batteries. In this example, the charging station is large enough to contain at least five batteries, and to simultaneously charge at least four batteries at the same time.

In FIG. 6, the first battery 112 is being removed from the charging station through the outlet 118, which is formed a horizontal slot above the base 126. The battery 112 entered the charging station first (before batteries 212, 312, 412, and 512) and exits first (ahead of batteries 212, 312, 412, 512). The shape of the housing 120 orients the batteries in this order, such that the batteries arrive at the outlet in the same order that they entered the inlet. This means that the battery that has spent the longest time in the charging station, and thus had the longest amount of time to receive charge, is the first one available to be taken for use.

In an embodiment, the housing 120 of the charging station is formed as a cabinet or bin that receives depleted batteries into the housing. The housing accepts the batteries through the inlet one at a time and keeps them in that order as they pass through the housing to the outlet.

Figure 7:
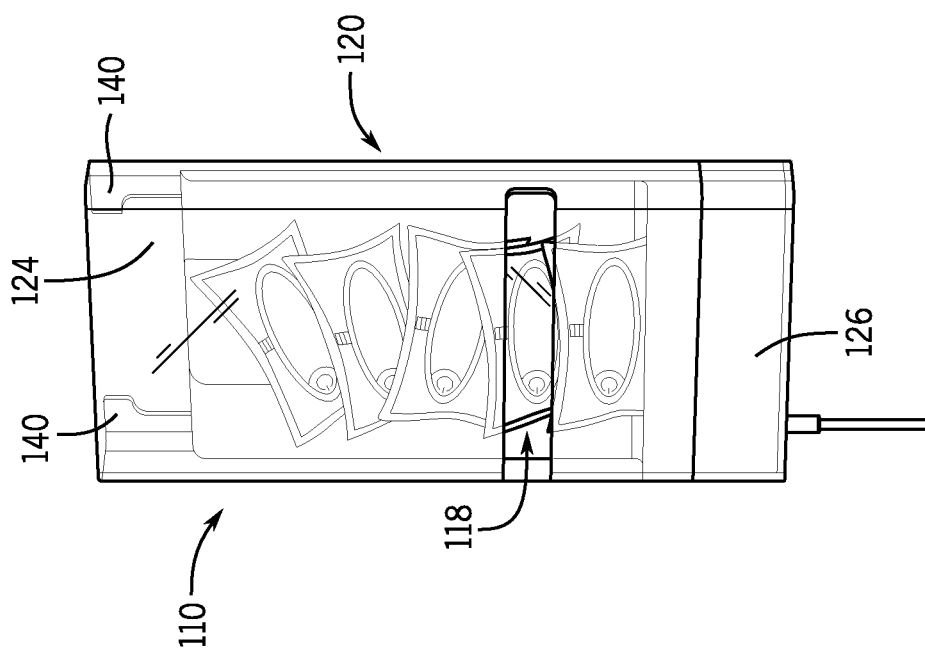
FIG. 7 is a perspective view of a wireless charging system with a sliding removable cover, according to an embodiment of the present disclosure.

FIGS. 7-8 show an embodiment in which the front cover 124 is slidable vertically along the housing 120. In FIG. 7, the front cover 124 slides up to expose the base 126, and in FIG. 8 the front cover 124 slides down to expose the top of the rear plate 122. In this embodiment, the front cover 124 includes an open top and an open bottom, so that it can slide in either direction. This sliding motion can be helpful to access either end of the housing 120 (such as the base 126 or the plate 122) for inspection or cleaning. In an embodiment, the front cover 124 is fully or partially transparent, so that the batteries 112 inside the charging station are visible through the front cover 124. As shown in FIG. 7, in an embodiment, the outlet 118 is formed as a cutout edge that creates a horizontal slot in the front cover 124.

Figure 9:
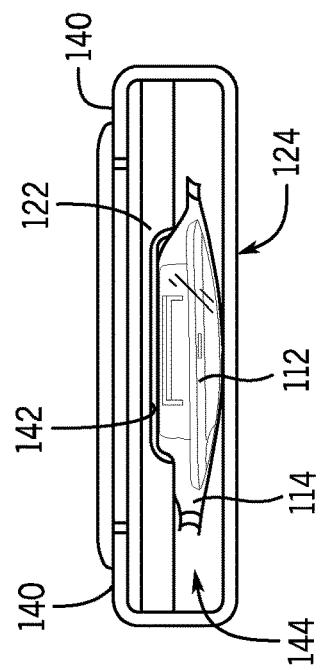
FIG. 9 is a top view of the wireless charging system of FIGS. 7-8.

A top view of the cover 124 and plate 122 is shown in FIG. 9. The cover 124 has a bracket shape with rear wings 140 that hook around the plate 122, to hold the cover 124 in place. FIG. 9 also shows the space formed between the rear plate 122 and the front cover 124, to accept the batteries 112 into the charging station. The space between the rear plate 112 and the front cover forms a channel 144 through the charging station. The channel 144 is sized and shaped to receive the batteries 112 in a horizontal orientation, so that multiple batteries can fit inside the charging station, forming a vertical stack of batteries along the channel 144. In an embodiment, the channel 144 is a vertical channel that extends along the vertical plate 122.

In an embodiment, the housing 120 includes a contoured surface 142 along the channel 144. In an example, the contoured surface 142 is the front surface of the rear plate 122. In this example, the contoured surface 142 widens in the middle, to accommodate the width of the batteries 112. The contoured surface 142 includes a recessed center, where the depth of the channel 144 increases. In an embodiment, the channel comprises has a vertical length, a horizontal width, and a depth perpendicular to the width, and the vertical length is longer than the horizontal width, and the horizontal width is longer than the depth. The depth of the channel increases in the recessed center. As shown in FIG. 9, this recess helps guide the batteries 112 into the channel 144 in a generally horizontal orientation.

Figure 10B:
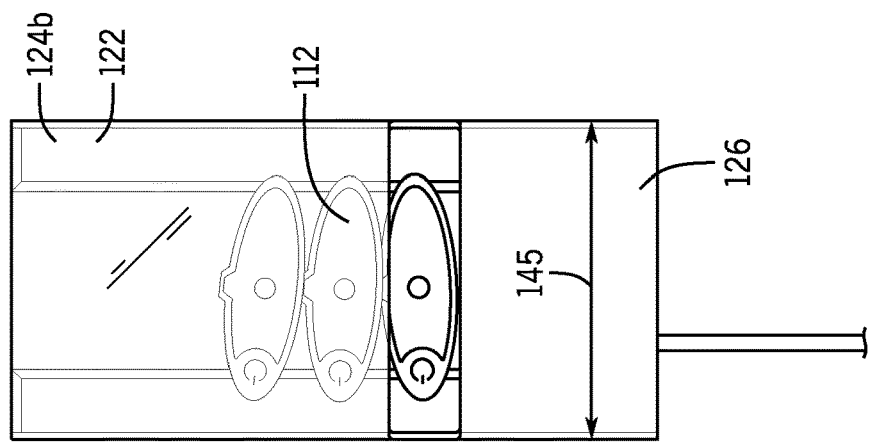
FIG. 10B is a front view of the wireless charging system with a removable cover that is sized to fit batteries that are not within a sterile barrier, according to an embodiment of the present disclosure.
Figure 10A:
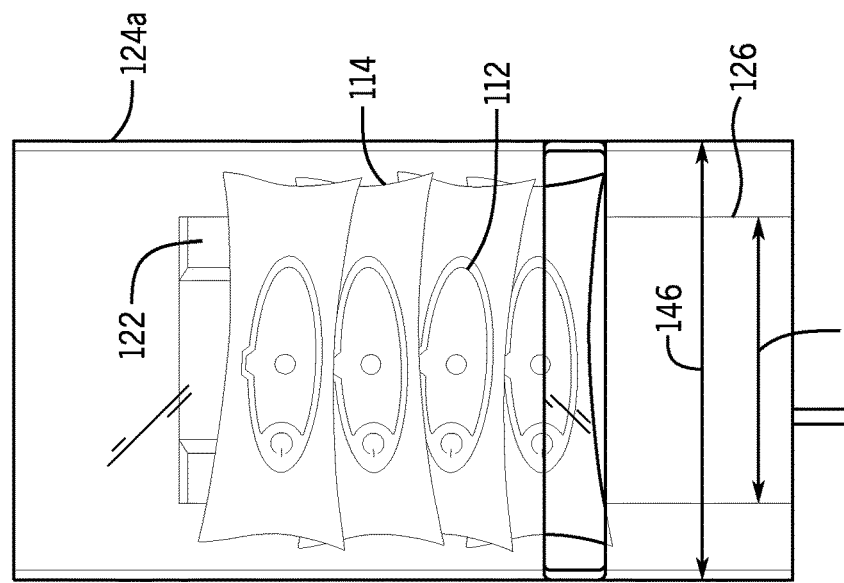
FIG. 10A is a front view of a wireless charging system with a removable cover that is sized to fit batteries sealed in a sterile barrier, according to an embodiment of the present disclosure.

The charging station 110 can be used to charge batteries 112 that are in sterile barrier 114 or that are not sterile and, therefore, have a smaller footprint. FIG. 10A shows a first arrangement of a configurable charging station 110 with a first cover 124a that is sized to accommodate the larger sealed batteries 112 within respsetive sterile barriers 114. The cover 124a fits over the base 126, which is generally smaller (narrower) than the cover 124a such that the first cover 124a extends beyond the lateral edges of the base 126. That is, a width 145 of the base 126 is less than a width 146 of the cover 124a. Removal of the larger cover 124a and replacement with a smaller cover 124b (FIG. 10B) transitions the charging station 110 to a second arrangement that is sized to better accommodate nonsterile batteries 112 that are not within sterile barriers 114. In an embodiment, the second cover 124b is about as wide as the width 145 of the base 126. The configurable charging station 110 can be provided as a kit with different covers 124a, 124b to be removed and replaced as desired by the user, depending on whether sterile or nonsterile batteries 112 are generally charged. It should be understood that both sterile and nonsterile batteries 112 fit within the cover 124a of the first arrangement.

Figure 12:
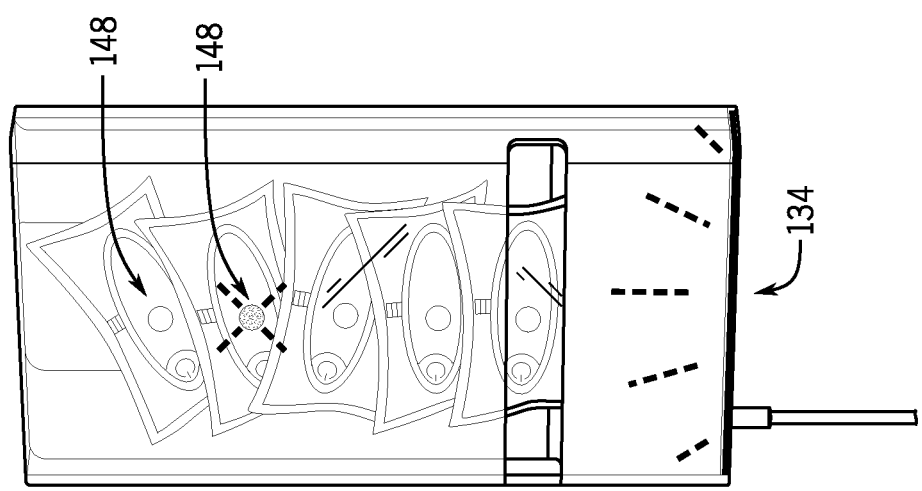
FIG. 12 is a perspective view of a wireless charging system with a status indicator, according to an embodiment of the present disclosure.
Figure 11:
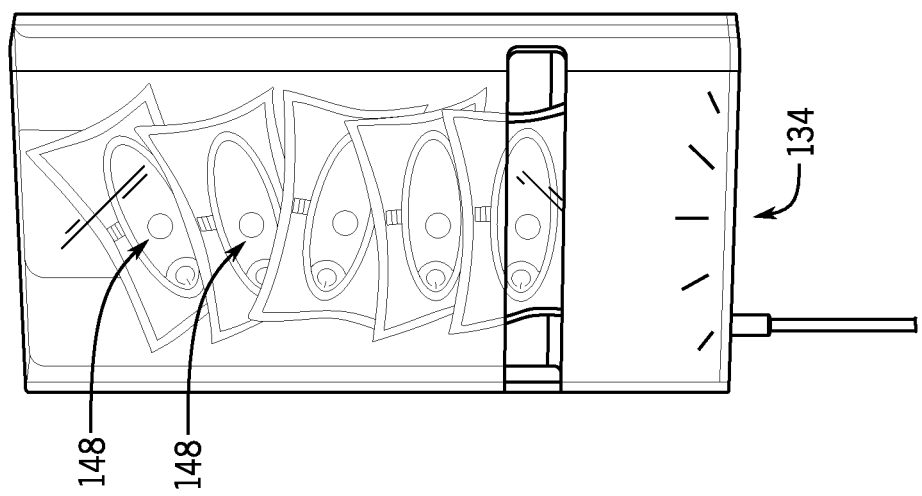
FIG. 11 is a perspective view of a wireless charging system with a status indicator, according to an embodiment of the present disclosure.

FIGS. 11-12 show different states of the indicator light 134. In FIG. 11, the indicator light 134 is illuminated in a first state, such as a solid first color. This first color can be white, green, blue, or other colors, and the solid state means the color is not blinking. This state of the indicator light means the charging station 110 is turned on and operating normally. In FIG. 12, the indicator light 134 has changed to a second color (such as red, orange, yellow, or other colors) and is flashing. This can indicate an error state, to alert users that the charging station 110 is not operating correctly. When the indicator light 134 is dark (not turned on), then that means that the charging station 110 is not powered on. Different combinations of colors, blinking patterns, and visible indications (brightness, etc.) correspond with various system states, to communicate information to the user.

In an embodiment, the batteries 112 also include an indicator light 146. This is a visible indicator that shows the state of charging of the batteries 112. A first state of the indicator 146 (color, blinking pattern, brightness, or combinations of visual indications) indicates that the battery is depleted and receiving power. A second state (different color, etc.) indicates that the battery is fully charged. A third state indicates that the battery is malfunctioning, or not charging correctly. A dark state indicates that the battery is not currently charging.

Figure 14:
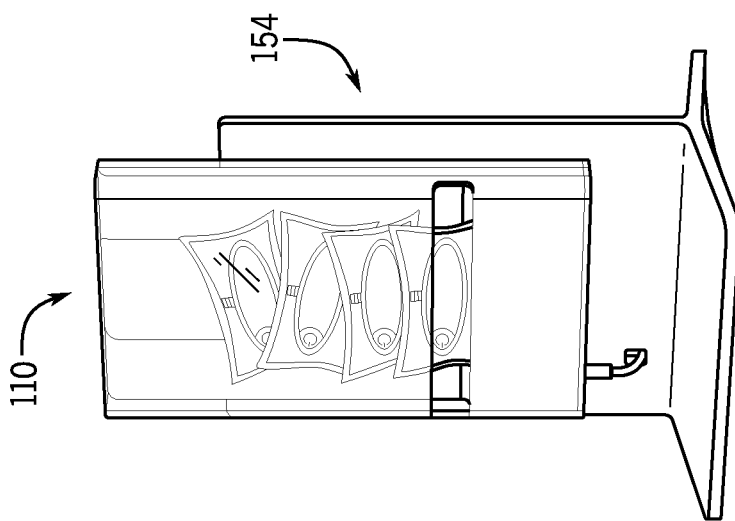
FIG. 14 is a front perspective view of a charging station with an upright stand, according to an embodiment of the present disclosure.
Figure 13:
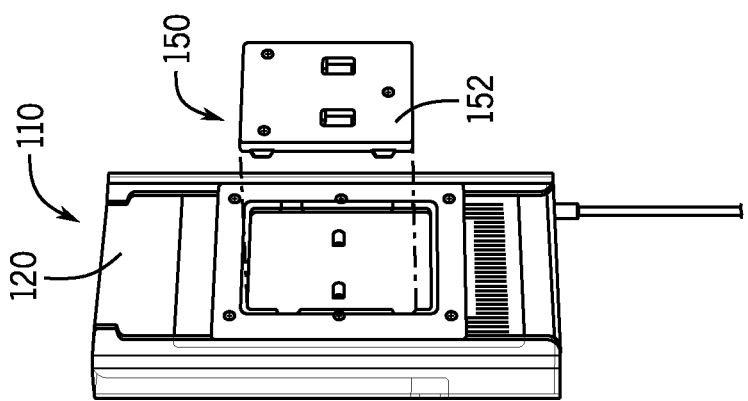
FIG. 13 is a rear view of a charging station with a wall mount, according to an embodiment of the present disclosure.

FIGS. 13-14 show two options for mounting the charging station 110 in a medical environment. FIG. 13 shows a wall mount 150 including a bracket 152 that attaches the housing 120 to a wall. FIG. 14 shows an upright stand or rack 154 that supports the housing 120 and can be placed on a horizontal surface such as a table or counter. These are two options for placing the charging station 110 in a medical environment such as a hospital, operating room, surgery centers, urgent care centers, clinical care centers, and others. While disclosed embodiments show a generally vertical mounting arrangement and with the channel 114 being oriented vertically (perpendicular to the floor), the charging station 110 may be mounted in other orientations, e.g., angled or horizontally. For example, in a horizontal mounting arrangement, the batteries 112 can be pushed through the channel 144.

Figure 15:
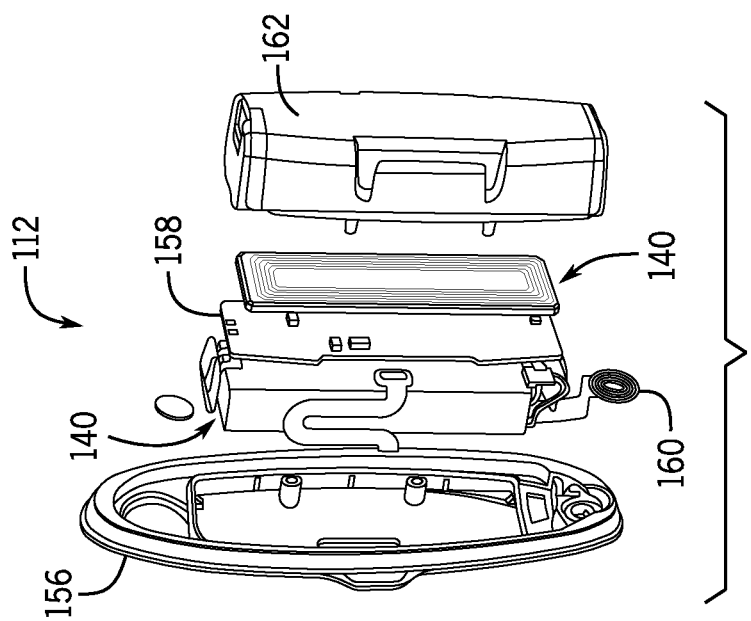
FIG. 15 is an exploded view of a rechargeable battery, according to an embodiment of the present disclosure.

FIG. 15 shows an exploded view of a chargeable battery 112, according to an embodiment. In an embodiment, the battery 112 is re-chargeable, meaning it can be charged again after is has been depleted. The battery 112 includes a power receiver 140 such as a printed circuit board with a power receiving antenna. The power receiver 140 is coupled to a battery cell 142, which stores the received power. In an embodiment, the battery cell 142 is a lithium cell. The battery 112 also includes a top case or cover 156, a main printed circuit board 158, a flex circuit 160, and a rear case or cover 162, among other components. In an embodiment, the indicator light 146 is an LED (light emitting diode) carried by the flex circuit 160 and visible through the front case 156.

Figure 16:
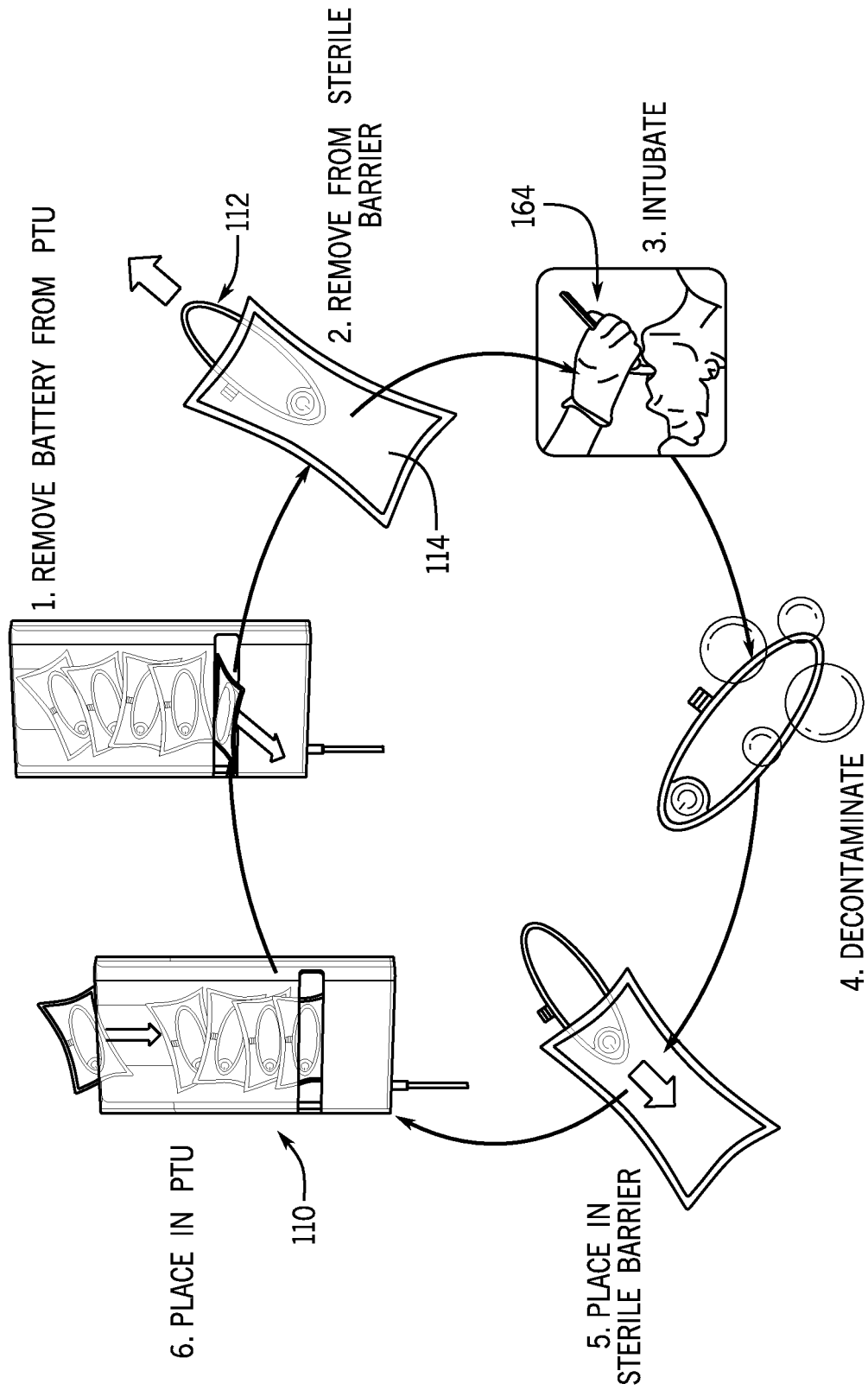
FIG. 16 is a schematic view of a method of wirelessly charging batteries, according to an embodiment of the present disclosure.

FIG. 16 shows a method for wirelessly charging batteries for a medical device, in this case a video laryngoscope. At number 1, a battery 112 is removed from the outlet of the charging station (also referred to as the power transmitting unit, PTU). At number 2, the battery 112 is removed from the sterile barrier 114, for insertion into a medical device. In the example of FIG. 16, the battery 112 is a battery 112for a video laryngoscope 164. At number 3, the battery 112 is inserted or plugged into the medical device (such as the video laryngoscope 164), and the medical professional (such as a doctor, therapist, nurse, or other practitioner) uses the medical device in a medical procedure (such as an intubation—inserting an endotracheal tube or other airway device into a patient's airway passages such as the trachea). In number 4, the battery 112 is decontaminated after use. In an example, the battery 112 is cleaned with a cleaning solution or is sterilized. In number 5, the cleaned battery 112 is placed inside a sterile barrier 114 and sealed. In number 6, the depleted battery 112 is placed back into the top of the charging station, where it passes through the charging field in the vertical stack of batteries 112 and receives power from the charging station 110. The battery 112 emerges at the outlet in a charged state, back at numeral 1 in FIG. 16, and the cycle repeats.

Batteries 112 can be received into the inlet in any state—charged, partially charged, or depleted. Depending on the particular environment where they are used, the batteries 112 may be fully depleted before they are decontaminated and returned to the charging station 110, or they may be only partially depleted. In the example of FIG. 16, an intubation performed with a video laryngoscope 164 may deplete the battery 112 only partially, and the battery 112 is then moved through steps 4, 5, and 6 and charged back to full in the charging station 110. If a particular video laryngoscopy 164 procedure takes a longer amount of time, for example, the battery 112 in use may be depleted further or fully depleted. The charging station 110 can accept batteries 112 in any of these conditions, for charging back to full.

In an embodiment, the sterile barrier 114 is a plastic or paper pouch that is sealed around the battery 112 such as by vacuum or heat sealing, creating a sterile single or double barrier with the battery inside. The barrier 114 is compatible with sterilization methods (such as chemical, temperature, or radiation methods) and does not block the magnetic charging field from the power transmitter 136.

According to an embodiment, a method is provided for wirelessly recharging batteries (e.g., batteries 112) inside a sterile barrier (e.g., sterile barrier 114). The method includes receiving a first battery in a depleted state through an inlet at a top of a charging station (e.g., charging station 110). The first battery is sealed inside a first sterile barrier. The method includes receiving a second battery in a depleted state through the inlet and onto the first battery to form a vertical stack of batteries inside the charging station. The second battery is sealed inside a second sterile barrier. The method includes transmitting power wirelessly to the first battery through the first sterile barrier and simultaneously transmitting power wirelessly to the second battery through the second sterile barrier, such that both batteries are charging at the same time. The method includes providing the first battery in a charged state through an outlet at a bottom of the charging station, and subsequently, providing the second battery in a charged state through the outlet.

Figure 17:
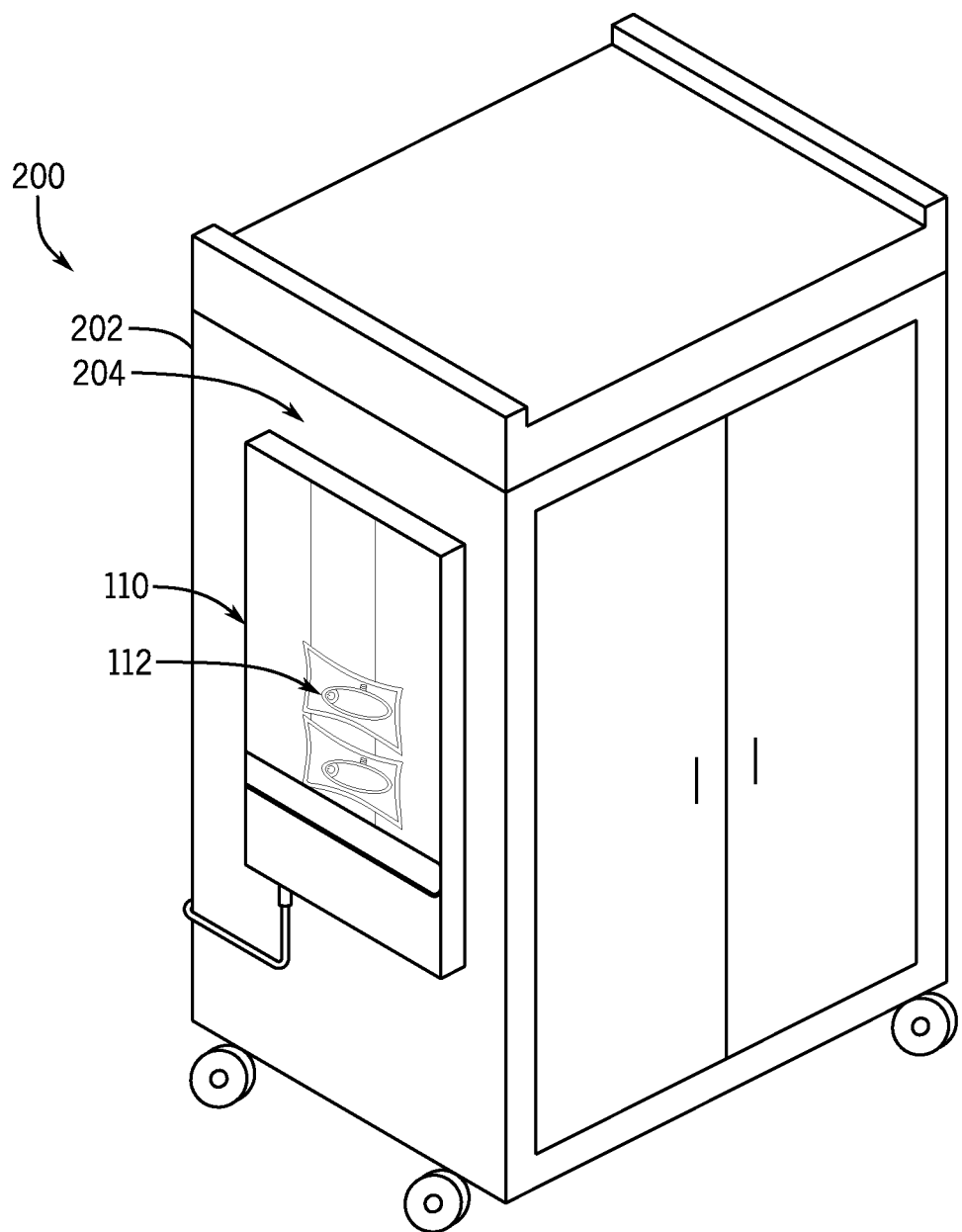
FIG. 17 is a front perspective view of a charging station mounted on a metal cabinet, according to an embodiment of the present disclosure.
Figure 18:
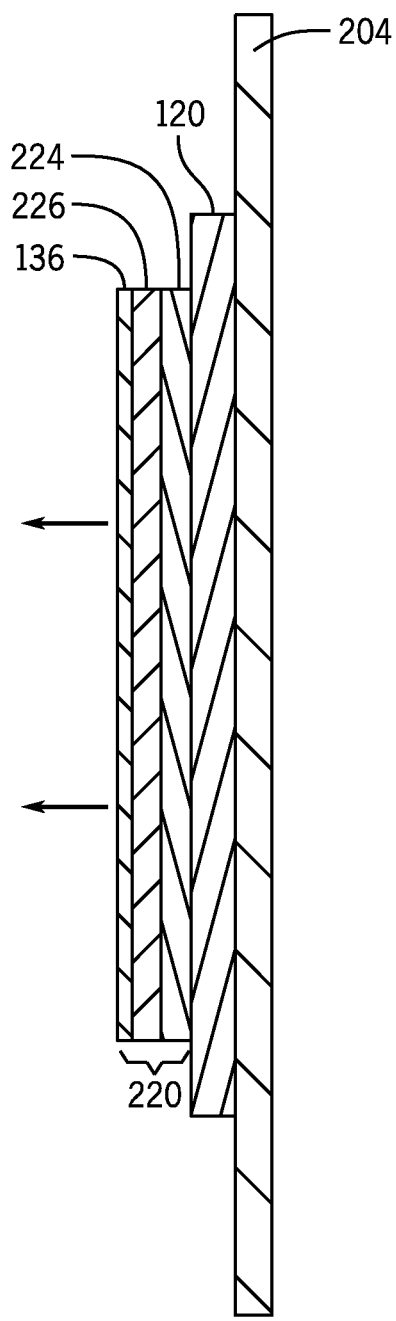
FIG. 18 is a cross-sectional view of components of a shielding arrangement for a charging station, according to an embodiment of the present disclosure.
Figure 19:
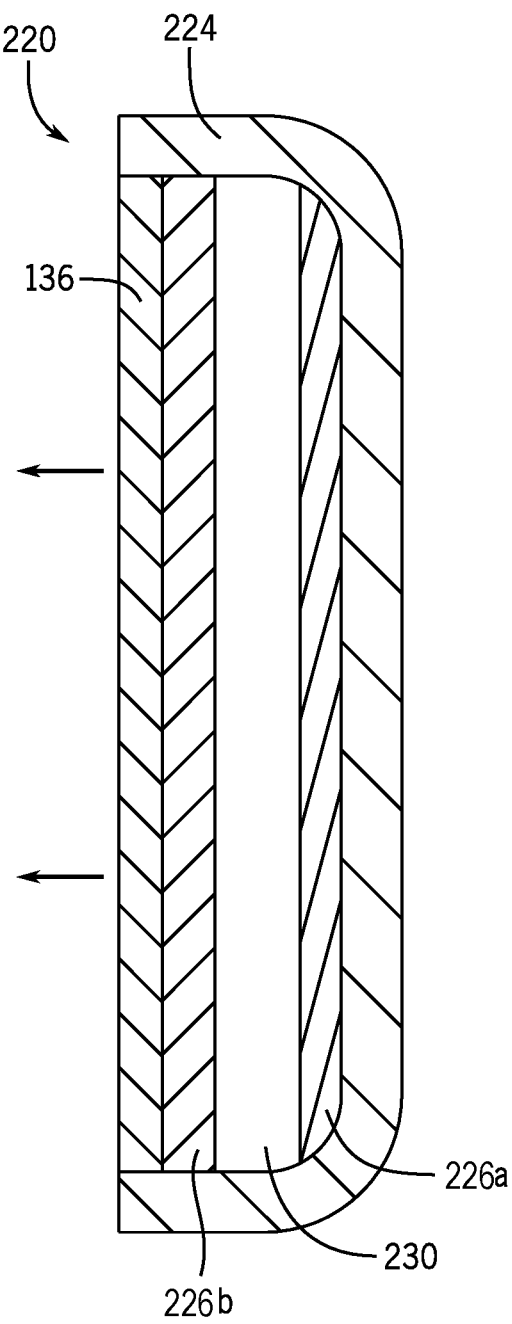
FIG. 19 is a cross-sectional view of components of a shielding arrangement for a charging station, according to an embodiment of the present disclosure.

The charging station 110 can be mounted as provided herein to a stand, surfaces or walls, or to equipment in a medical environment. FIG. 17 shows a charging station system 200 in which the charging station 110 is mounted on (e.g., mounted directly on, coupled to) a medical cabinet 202. The charging station 110 may be close to or in direct contact with a metal surface 204 of the medical cabinet 202, and the metal surface 202 can act as a power drain on the charging field generated by the power transmitter 136 (FIG. 3) of the charging station 110. FIGS. 18-19 show examples of shielding arrangements for the charging station 110 that prevent or reduce power drains away from charging batteries 112 that may be caused by metallic mounting surfaces positioned close to a power transmitter.

FIG. 18 is a cross-sectional view of a mounted charging station 110 of the system 200. The metal surface 204 is directly coupled to the housing 120 of the charging station 110. However, it should be understood that other mounting arrangements may involve intervening mounting brackets or structures positioned between the housing 120 and the metal surface 204. To facilitate transmission of the charging field of the power transmitter 136 towards any inserted batteries 112, shown by the arrows, one or more shielding layers are positioned between the power transmitter and the metal surface 204 to form a shielded power transmitter assembly 220. The shielding arrangement prevents a drain of the charging field in the direction of the metal surface 204, or a drain in a direction opposite the desired direction of the charging field. Therefore, the charging field is emitted in the direction of the inserted batteries 112.

In an embodiment, the shielded power transmitter assembly 220 includes a non-ferromagnetic layer 224 separated from the power transmitter 136 by a ferrite or ferromagnetic layer 226. The non-ferromagnetic layer 224 may be a non-ferromagnetic metal, such as gold, silver, platinum, aluminum, copper, nickel, zinc, titanium, or combinations thereof. The non-ferromagnetic layer 224 may be a graphite layer. The ferrite or ferromagnetic layer 226 may be a ferrite or ferrous iron, cobalt, or nickel. The ferrite or ferromagnetic layer 226 may be in direct contact with a surface of the power transmitter opposing the direction of the charging field.

FIG. 19 is view of an embodiment of the shielded power transmitter assembly 220 that includes a curved non-ferromagnetic layer 224. The assembly 220 also includes a first ferrite or ferromagnetic layer 226a and a second ferrite or ferromagnetic layer 226b separated by an air gap 230. The power transmitter 136 is, in the depicted embodiment, adjacent to the second ferrite or ferromagnetic layer 226b.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A wireless charging system for recharging batteries in a medical environment, comprising:
    a charging station comprising:
        a housing comprising a rear plate, a slidable front cover, and a base;
        an inlet for depleted batteries at a top of the housing, wherein the inlet comprises an opening between the rear plate and the slidable front cover;
        an outlet for charged batteries below the inlet, wherein the outlet comprises a slot in the slidable front cover;
        a vertical channel extending between the inlet and outlet;
        a wireless power transmitter inside the rear plate, wherein the wireless power transmitter comprises a transmitting antenna having a vertical length that is longer than a horizontal width and sized to charge at least two rechargeable batteries simultaneously in different orientations;
        a status light on the housing; and
        a power supply connected to the housing; and
    at least two rechargeable batteries in different orientations inside the vertical channel, each battery having a wireless power receiver which comprises a receiving antenna.

2. The wireless charging system of claim 1, wherein the charging station comprises a shielded wireless power transmitter assembly comprising:
    the wireless power transmitter;
    a non-ferromagnetic layer; and
    at least one ferrite or ferromagnetic layer.

3. The wireless charging system of claim 2, wherein the wireless power transmitter is positioned between the at least one ferrite or ferromagnetic layer and the at least two rechargeable batteries.

4. The wireless charging system of claim 1, wherein the slidable front cover is transparent.

5. The wireless charging system of claim 1, wherein the at least two rechargeable batteries form a vertical stack.

6. A wireless charging system for recharging batteries in a medical environment, comprising:
    a charging station comprising:
        a housing comprising a rear plate, a front cover, and a base;
        an inlet of the housing for depleted batteries;
        an outlet for charged batteries, wherein the outlet comprises a slot in the housing;
        a channel extending between the inlet and outlet; and
        a wireless power transmitter inside the rear plate, the wireless power transmitter sized to simultaneously charge at least two rechargeable batteries in different orientations; and
    at least two rechargeable batteries in different orientations inside the channel, each battery having a wireless power receiver.

7. The wireless charging system of claim 6, the front cover is removable, and wherein the channel is formed between the removable front cover and the rear plate.

8. The wireless charging system of claim 7, wherein the removable front cover is transparent and is slidable vertically along the rear plate.

9. The wireless charging system of claim 6, wherein the channel comprises a vertical length, a horizontal width, and a depth perpendicular to the width, and wherein the vertical length is longer than the horizontal width, and wherein the horizontal width is longer than the depth.

10. The wireless charging system of claim 6, wherein the charging station further comprises a status light that comprises at least one of an illuminated surface, an illuminated horizontal bar, or an illuminated vertical bar.

11. The wireless charging system of claim 6, wherein the inlet comprises an opening between the rear plate and the front cover, and wherein the outlet comprises a slot in the front cover.

12. The wireless charging system of claim 10, wherein the outlet comprises a horizontal slot at a bottom of the channel.

13. A wireless charging station for recharging batteries in a medical environment, comprising:
    a housing comprising a rear plate, a front cover, and a base;
    an inlet for depleted batteries at a top of the housing, wherein the inlet comprises an opening between the rear plate and the front cover;
    an outlet for charged batteries below the inlet, wherein the outlet comprises a slot in the front cover;
    a vertical channel extending between the inlet and outlet;
    a wireless power transmitter inside the rear plate, wherein the wireless power transmitter comprises a transmitting antenna having a vertical length that is longer than a horizontal width and sized to charge at least two rechargeable batteries simultaneously in different orientations;
    a status light on the housing; and
    a power supply connected to the housing.

14. The charging station of claim 13, further comprising a wall mount including a bracket attachable to a wall.

15. The charging station of claim 13, wherein the front cover is slidable.

* * * * *